(12) United States Patent
Rezvani et al.

(10) Patent No.: US 8,063,644 B2
(45) Date of Patent: Nov. 22, 2011

(54) IMPEDANCE MEASUREMENT OF A PH ELECTRODE

(75) Inventors: Behzad Rezvani, Anaheim, CA (US); Jeffrey Lomibao, Corona, CA (US); Chang-Dong Feng, Long Beach, CA (US)

(73) Assignee: Rosemount Analytical Inc., Irvine, CA (US)

( * ) Notice: Subject to any disclaimer, the term of this patent is extended or adjusted under 35 U.S.C. 154(b) by 495 days.

(21) Appl. No.: 11/894,038

(22) Filed: Aug. 17, 2007

(65) Prior Publication Data

US 2008/0042665 A1 Feb. 21, 2008

Related U.S. Application Data

(60) Provisional application No. 60/838,793, filed on Aug. 18, 2006, provisional application No. 60/845,491, filed on Sep. 18, 2006.

(51) Int. Cl.
*G01N 27/416* (2006.01)

(52) U.S. Cl. ..................................... 324/438

(58) Field of Classification Search .................. 324/438
See application file for complete search history.

(56) References Cited

U.S. PATENT DOCUMENTS

| | | | |
|---|---|---|---|
| 4,189,367 A | 2/1980 | Connery et al. | 204/195 |
| 4,780,664 A * | 10/1988 | Ansuini et al. | 324/700 |
| 5,256,894 A * | 10/1993 | Shino | 257/388 |
| 5,268,852 A | 12/1993 | Forsythe et al. | 364/482 |
| 5,469,070 A | 11/1995 | Koluvek | 324/713 |
| 6,168,948 B1 * | 1/2001 | Anderson et al. | 435/287.2 |
| 6,429,660 B1 | 8/2002 | Rezvani | 324/426 |
| 6,556,020 B1 * | 4/2003 | McCabe et al. | 324/426 |
| 2006/0042961 A1 * | 3/2006 | Mu | 205/775 |
| 2007/0208233 A1 * | 9/2007 | Kovacs | 600/300 |

FOREIGN PATENT DOCUMENTS

| | | |
|---|---|---|
| EP | 0 419 769 | 4/1991 |
| GB | 2 296 332 | 6/1996 |

OTHER PUBLICATIONS

"Glass electrode," http://en.wikipedia.org/wiki/PH_glass_electrode, Jun. 1, 2007, 3 pages.
"Basics of pH Control," Rosemount Analytical Application Data Sheet ADS43-001/rev. A, Aug. 2004, 4 pages.
"The Theory of pH Measurement," Rosemount Analytical Application Data Sheet ADS 43-002/rev. A, Aug. 2004, 8 pages.
Buck, R.P., "Transient electrical behavior of glass membrances," J. Electroanal.Chem., vol. 18, 1968, p. 381-386.

(Continued)

*Primary Examiner* — Jeff Natalini
(74) *Attorney, Agent, or Firm* — Christopher R. Christenson; Westman, Champlin & Kelly, P.A.

(57) ABSTRACT

A method of measuring impedance of a pH electrode is provided. A test current is applied to the pH electrode for a time duration that is less than 50 percent of a time constant that is associated with electrical characteristics of the pH electrode. A voltage response of the pH electrode is measured when the test current is applied to the pH electrode. An impedance of the pH electrode is calculated as a function of the voltage response.

11 Claims, 5 Drawing Sheets

OTHER PUBLICATIONS

Han, W-T et al., "Complex impedance analysis of the glass/solution interface in the glass electrode for pH measurement," Journal of Non-Crystalline Solids, vol. 203, Aug. 1996, p. 345-352.

Moody et al., "Mechanistic studies of ion-selective electrodes," Journal of Biomedical Engineering, vol. 7, Jul. 1985, p. 183-195.

Shervedanie, R. K. et al., "Electrochemical characterization and application of Ni-Ru02 as a pH sensor for determination of petroleum oil acid number," J. Iranian Chemical Society, vol. 4, No. 2, Jun. 2007, p. 221-228.

Search Report and Written Opinion from corresponding international application PCT/US2007/018383, filed Aug. 17, 2007.

* cited by examiner

IMPEDANCE MEASUREMENT OF A PH ELECTRODE

CROSS-REFERENCE TO CO-PENDING APPLICATION

The present application is based on and claims the benefit of U.S. provisional patent application Ser. No. 60/838,793, filed Aug. 18, 2006, and U.S. provisional patent application Ser. No. 60/845,491, filed Sep. 18, 2006, the contents of which applications are hereby incorporated by reference in their entirety.

BACKGROUND pH is a measure of the acidity or alkalinity of a solution and can be determined using a pH-selective electrode (for instance, pH glass electrode, hydrogen electrode, quinhydrone electrode, ion sensitive field effect transistor). pH sensors measure ion content and are often utilized in industrial process control systems to measure the hydrogen ($H^+$) or hydroxyl ($OH^-$) ion content of a solution.

pH sensors commonly employ at least two electrodes, an ion-specific electrode (a pH electrode) and a reference electrode. In one example, a pH electrode utilizes a pH sensitive glass, in contact with a solution, which develops a potential (voltage) proportional to the pH of the solution. A reference electrode provides a known reference potential for the pH electrode. The difference in the potentials of the pH electrode and the reference electrodes provides a millivolt signal proportional to pH.

Over time, pH electrodes can experience aging which can result in changes to the electrical characteristics of the electrode. Electrode aging may be caused and/or accelerated by, for example, use in high temperatures, operation of the pH electrode in process media or solutions that have either high acidity or alkalinity, or incorrect handling of the pH electrode when not in use, e.g. incorrect cleaning and storage procedures. Electrode aging can cause an increase in impedance and response time, a declining slope, especially in the alkaline region, and/or a shift of the asymmetry potential, for example. Further, electrode aging can be indicative of changes in the chemical composition of the membrane glass, steady growth of the internal membrane gel layer, and/or chemically and mechanically induced degradation of the outer gel layer of the membrane during measurement and cleaning. As an electrode deteriorates, the ability of the sensor to accurately measure pH also deteriorates resulting in inaccurate and/or inconsistent pH level measurements.

SUMMARY

A method is provided for measuring impedance of a pH electrode. The method includes applying a test current to the pH electrode for a time duration that is less than 50 percent of a time constant that is associated with electrical characteristics of the pH electrode, measuring a voltage response of the pH electrode when the test current is applied to the pH electrode, and calculating an impedance of the pH electrode as a function of the voltage response.

These and various other features and advantages will be apparent from a reading of the following Detailed Description using the exemplary embodiment therein described. This Summary and Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

DETAILED DESCRIPTION

The concepts described herein relate to measuring electrical characteristics of a sensor, which can be useful for diagnostic and maintenance purposes. For instance, in one embodiment a change in electrode impedance can be utilized to decide whether a sensor needs to be re-calibrated or replaced. It should be understood that while the concepts described herein are described with reference to a pH sensor, these concepts are applicable to other types of sensors, such as selective ion sensors, oxygen sensors, to name a few.

Figure 1:
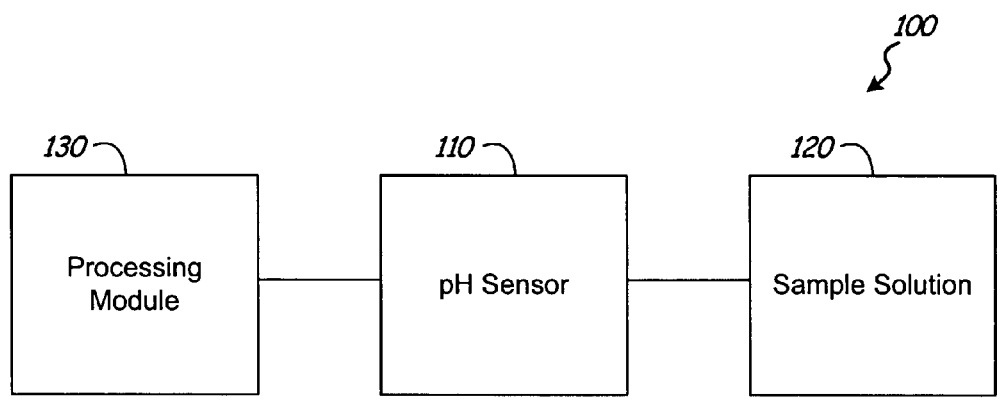
FIG. 1 is a block diagram of an exemplary pH measuring system.

First, it may be useful to describe an exemplary environment and system for measuring pH of a solution. As illustrated in FIG. 1, an exemplary pH measuring system 100 includes a pH sensor 110 configured to measure a pH of a solution 120. Solution 120 can be, for example, a mixture within an industrial process. pH sensor 110 produces a signal, indicative of a pH of solution 120, which can be provided to processing module 130. In one example, processing module 130 is configured to provide a visual display indicative of the pH measurement and/or to control a process based on the pH measurement. For example, processing module 130 can include a control system that controls addition of a neutralizing agent to solution 120 to maintain solution 120 at a predetermined pH (e.g., a pH of neutrality or within certain limits).

Figure 2:
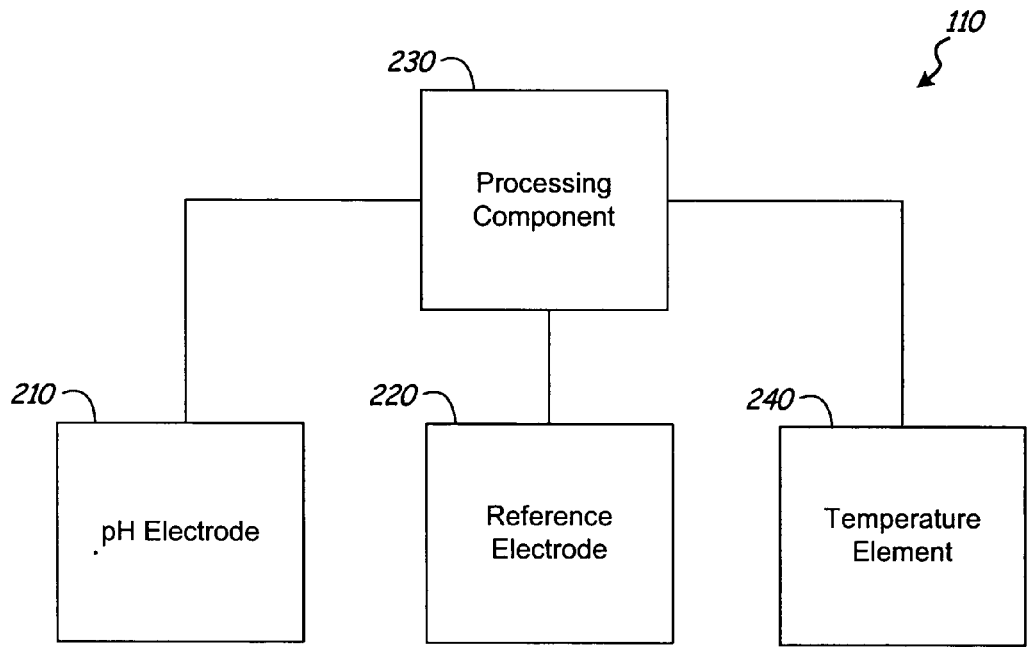
FIG. 2 is a diagrammatic view of an exemplary pH sensor.

FIG. 2 is a diagrammatic view of exemplary pH sensor 110. Sensor 110 includes a pH electrode 210 and a reference electrode 220. pH electrode 210 is configured to develop a potential (voltage) proportional to the pH of a solution, such as solution 120 in FIG. 1. Reference electrode 220 maintains a known reference potential for the pH electrode 210. The signals from pH electrode 210 and reference electrode 220 are provided to a processing component 230. Component 230 is configured to receive the signals from the electrodes and determine a pH based on the signals. In one embodiment, the difference in the potentials of the pH electrode 210 and reference electrode 220 provides a millivolt signal proportional to pH level. Sensor 110 is calibrated such that there is a known relationship between the potentials of the pH electrode 210 and reference electrode 220 when the sensor 110 is in a neutral solution (i.e., pH=7). For example, in one embodiment sensor 110 is calibrated by adjusting component 230.

Component 230 can include a display, for example an LCD, to provide a visual indication of the pH measurement.

Further, component 230 can be configured to communicate with a control system, such as processing module 130 in FIG. 1.

In some embodiments, measurement of pH is temperature dependent. A temperature element 240 can be provided to measure a temperature of the solution for which pH level is being determined. Processing component 230 can utilize the signal from temperature element 240 to compensate the pH measurement accordingly.

Over time, electrode deterioration can result in changes to the electrical characteristics of the electrode (i.e., impedance) which can affect sensor measurements. For instance, electrodes such as those of pH sensors immersed in solutions can become coated over time, which can cause an increase in electrode resistance. Electrodes can also become cracked or broken which can cause a sharp decrease in electrode resistance.

Calculating electrode impedance allows the integrity of the sensor and relative accuracy of the system to be determined. For instance, diagnostic tests performed on sensor 110 can be utilized to determine whether pH electrode 210 and/or reference electrode 220 has deteriorated such that replacement and/or re-calibration are required. Processing component 230 can be configured to perform diagnostic operations by applying a signal to the pH electrode 210 (or reference electrode 220) to identify electrical characteristics of the electrode. In other embodiments, an external diagnostic tool can be utilized.

The system can be configured to generate a fault signal if the impedance of a sensor electrode reaches a predetermined threshold level. For example, the fault signal can be indicative of the electrode impedance reaching a maximum or minimum allowable resistance. The fault signal can be utilized to indicate that replacement, maintenance, and/or re-calibration is necessary.

In conventional systems, to test an electrode a signal is applied to the electrode and a response of the electrode is measured. The diagnostic tests are performed by injecting a known current into the electrode and measuring a stable voltage level across the sensor. This voltage response can be utilized to determine resistive characteristics of the sensor. However, because of the electrical characteristics of the electrode, a sufficient DC measurement in these conventional systems requires a wait time of approximately 20-30 seconds. During this measurement period pH readings are not updated. This long update rate is not acceptable in many applications.

The concepts described herein for measuring impedance of a pH electrode are based on the appreciation that the pH electrode forms a constant phase element that can be approximated by an RC circuit having a long time constant. Further, these concepts are based on the recognition that the electrical characteristics of the pH electrode can be approximated with a simplified circuit equivalent and diagnostic measurements can be obtained from the pH electrode during a time duration (e.g., 1-2 seconds, for instance) that is significantly shorter than a time constant associated with the pH electrode.

Figure 3:
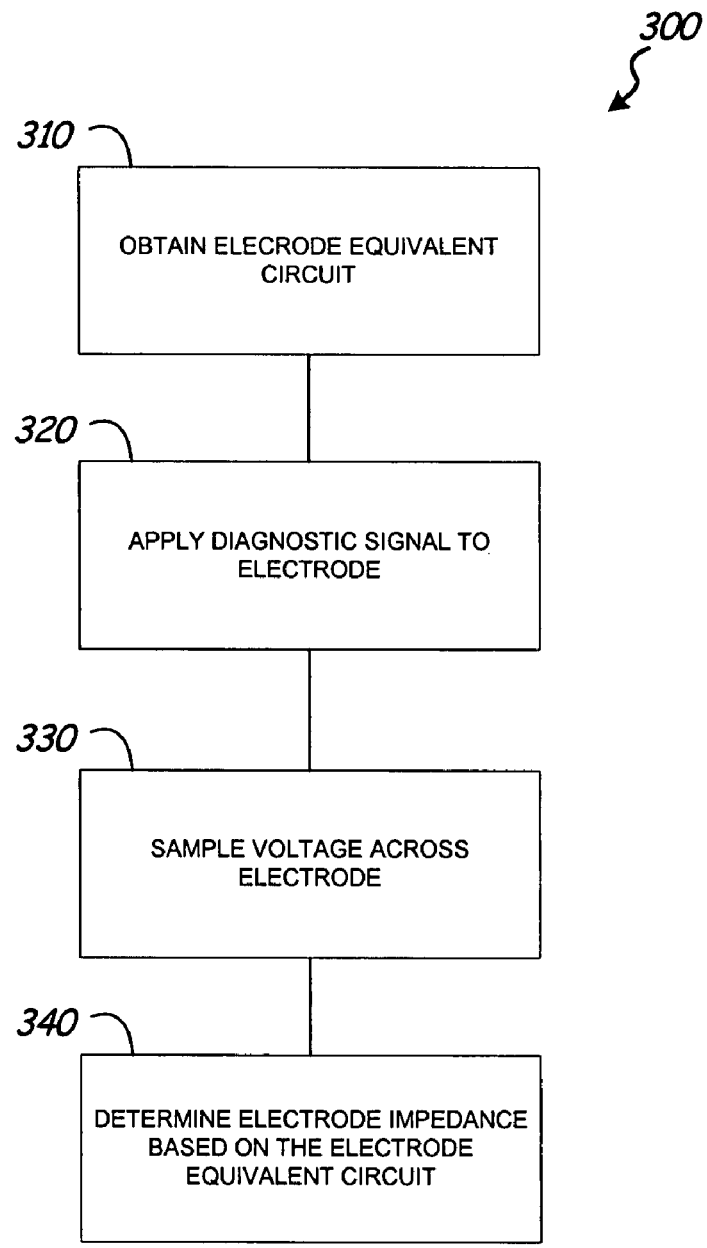
FIG. 3 is a flow diagram of a method for determining impedance of an electrode.

FIG. 3 illustrates a method 300 for measuring impedance of a pH electrode in accordance with one embodiment of the present invention. At step 310, an equivalent circuit is obtained based on the electrical characteristics of the electrode. At step 320, a diagnostic test signal is applied to the pH electrode. In one embodiment, a known DC test current is injected into the pH electrode. In one embodiment, the test current is a series of alternating DC test currents that are applied to the electrode being diagnosed. For example, a first test current at a known level is injected into the sensor. Then, a second test current that is substantially equal to but opposite in polarity to the first test current is injected into the sensor. At step 330, a voltage response of the electrode is measured across the electrode. In one embodiment, a series of voltage samples are taken across the electrode. The sampled data is utilized at step 340 to determine electrical impedance of the electrode that can be indicative of aging or degradation of the electrode.

Further, the sampled data can be utilized to determine a source voltage produced by the sensor. The source voltage is a signal representing a parameter or condition that the sensor is measuring. In one embodiment, the source voltage is indicative of the pH level of the solution being measured by the sensor.

Figure 4:
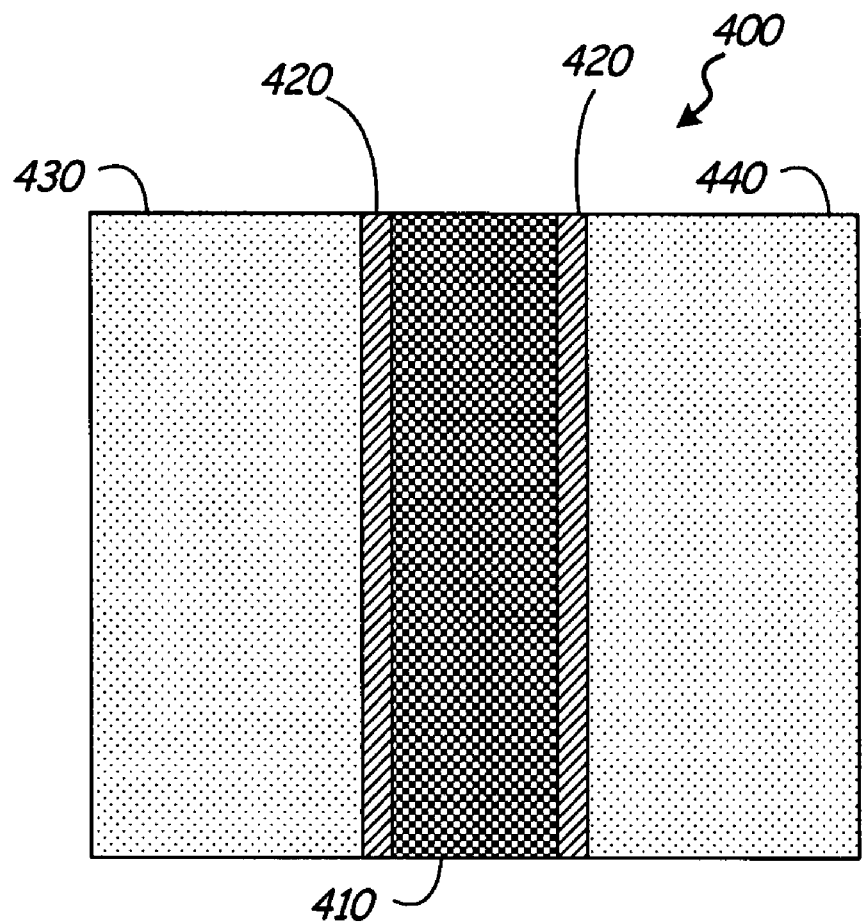
FIG. 4 illustrates a cross-section of a portion of an exemplary pH electrode.

Method 300 will now be described with respect to an exemplary pH electrode 400, illustrated in FIG. 4. In FIG. 4, a cross-section of a portion of exemplary pH electrode 400, such as pH electrode 210 in FIG. 2, is shown. pH electrode 400 includes a bulk layer 410 and a solution junction layer 420. In one embodiment, bulk layer 410 comprises a glass membrane. Further, junction layer 420 can comprise a gel layer formed on a surface of bulk layer 410. The gel layer can be, for example, a hydrated gel that selectively enables passage of ions therethrough. For purposes of this discussion, bulk layer 410 will be referred to hereinafter as glass membrane 410 and solution-junction layer 420 will be referred to as gel layer 420. However, it is noted that any suitable materials and configurations of electrode 400 are within the scope of the concepts described herein.

As illustrated, gel layer 420 can be formed on both sides of glass membrane 410. Glass membrane 410 and gel layers 420 separate a sample solution 430, for which pH measurement is desired, and a reference solution 440 having a known pH level. During pH measurement, pH electrode 400 develops a potential proportional to the pH of solution 430. A reference electrode (not shown in FIG. 4) can be utilized to provide a reference potential for the pH electrode 400.

Figure 5:
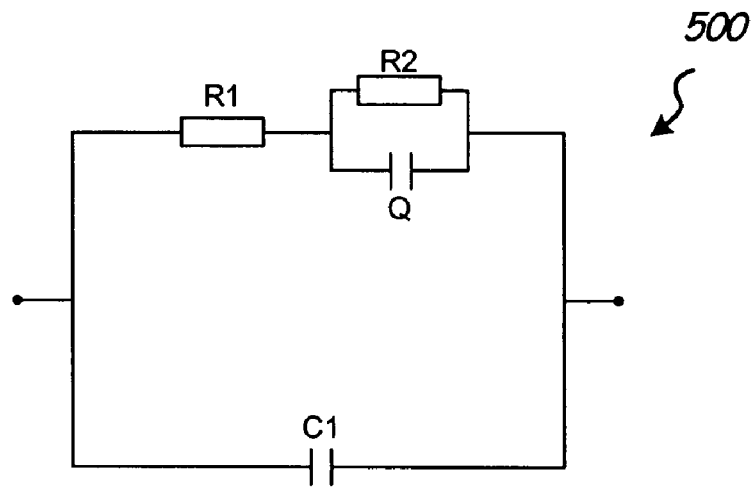
FIG. 5 illustrates an equivalent circuit corresponding to the electrical characteristics of the pH electrode of FIG. 4.

To calculate impedance of pH electrode 400 using method 300, a circuit equivalent of electrode 400 is obtained at step 310. Accordingly, FIG. 5 illustrates an equivalent circuit 500 corresponding to the electrical characteristics of pH electrode 400. In FIG. 5, C1 represents the capacitance formed by the glass membrane 410 as the dielectric. R1 is the electric resistance of the glass membrane 410. R2 is the electric resistance of the gel layer 420 and Q is the constant phase element of the gel layer 420 representing the transportation properties of ions through the gel layer 420. The total impedance of the pH electrode is approximately the sum of the solution junction layer (i.e., gel layer 420) impedance and the bulk layer (i.e., glass membrane 410) impedance.

Figure 6:
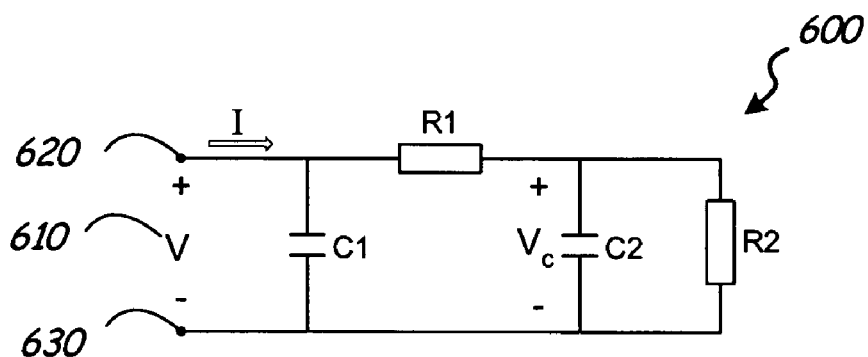
FIG. 6 illustrates an approximated equivalent circuit of the pH electrode of FIG. 4.

Based on experimental simulation values, it was determined that the resistive component R2 of gel layer 420 is the primary aging component of pH electrode 400. Thus, diagnosis of the pH electrode 400 substantially relies on the measurement of the electrical characteristics of the solution junction layer (i.e., gel layer 420). Since R2 is in connection with Q, a constant phase element (CPE), in parallel, and since Q is a significantly more complex component, it was appreciated that finding a measurement solution of R2 can be simplified by approximating Q. In particular, based on the experimental simulation values it was determined that constant phase element Q has an n value larger than 0.5. Therefore, constant phase element Q can be approximated by replacing Q with a capacitance. Accordingly, FIG. 6 illustrates an approximated equivalent circuit 600 of electrode 400 where the solution junction layer (i.e., gel layer 420) has been approximated by an RC network comprising a nonzero-frequency component C2 and a zero-frequency component R2. Equivalent circuit 600 has a time constant $R_2 \cdot C_2$ that is indicative of the electrical characteristics of the pH electrode 400. In other words, time constant $R_2 \cdot C_2$ characterizes the response of pH electrode 400. In one embodiment, time constant $R_2 \cdot C_2$ associated with electrode 400 is in the order of 7-8 seconds.

Based on the simplified circuit equivalent 600, the voltage across terminals 620 and 630 when a test current I is applied is given by the following equation:

$$V = IR_1 + (IR_2 - V_{c0})(1 - e^{-t/R_2 C_2}) + V_{c0} \quad \text{(Eq. 1)}$$

where $V_{c0}$ is the initial voltage (i.e., at time $t_0$) across nonzero-frequency component C2. Further, the initial voltage $V_{c0}$ is given by the formula:

$$V_{c0} = V_0 + IR_1 \quad \text{(Eq. 2)}$$

where $V_0$ is the initial voltage V across terminals 620 and 630. Thus, substituting Eq. 2 into Eq. 1 gives:

$$V = 2IR_1 + V_0 + (IR_2 - V_0 - IR_1)(1 - e^{-t/R_2 C_2}) \quad \text{(Eq. 3)}$$

$$dV/dt = \frac{1}{R_2 C_2}(IR_2 - V_0 - IR_1)e^{-(t_1+t_2)/2R_2 C_2} \quad \text{(Eq. 4)}$$

As discussed above, the resistive component R2 of gel layer 420 is the primary aging component of pH electrode 400. Thus, diagnosis of the pH electrode 400 substantially relies on the measurement of the electrical characteristics of the solution junction layer (i.e., gel layer 420). Therefore, Eq. 3 and 4 can be utilized to compute an equation for zero-frequency component R2 and nonzero-frequency component C2 of the electrode. From Eq. 3 and 4, the following equations are generated:

$$\frac{\Delta V_1/\Delta t_1}{\Delta V_2/\Delta t_2} = e^{-(t_3+t_1)/2R_2 C_2} \quad \text{(Eq. 5)}$$

If $\Delta t_1 = \Delta t_2 = \Delta t$, Eq. 5 gives:

$$R_2 C_2 = \Delta t / (\ln \Delta V_1 / \Delta V_2) \quad \text{(Eq. 6)}$$

Further, because the primary aging component of the pH electrode is the zero-frequency resistive component R2, it is advantageous to select an arbitrary value for nonzero-frequency component C2. In accordance with one embodiment, component C2 is approximated by an arbitrary value K. The arbitrary value K is, in one embodiment, ascertained based on experimental simulation values. In one example, K is set to a value of approximately 10 nF. However, it is noted that any arbitrary value can be selected based on the characteristics of the particular pH electrode being tested. Additionally, the methods and calculations explained herein can be applied to any suitable equivalent circuit with substantial exponential response to a constant current excitation.

Figure 7:
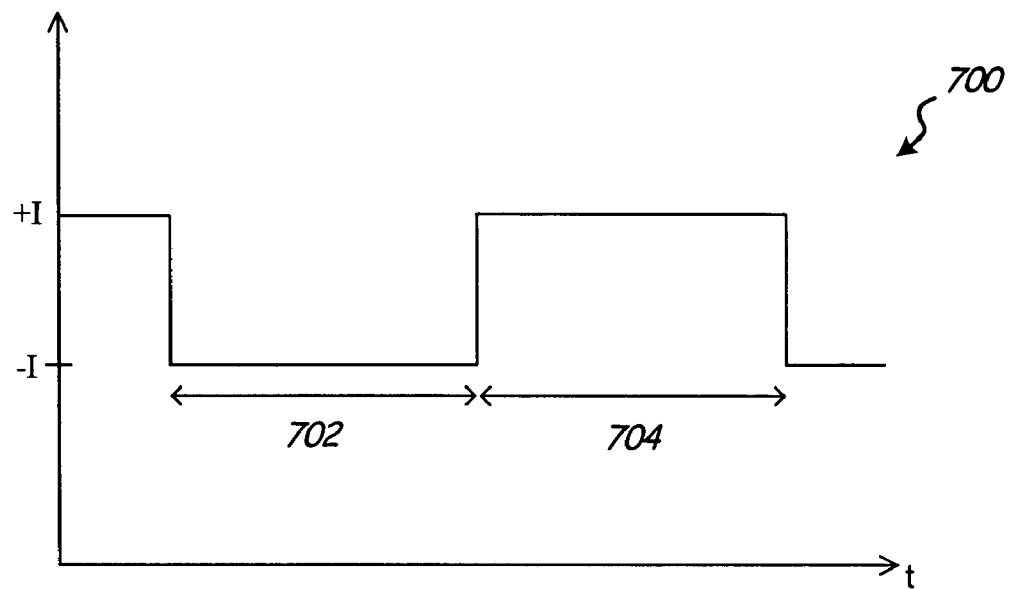
FIG. 7 illustrates one embodiment of a diagnostic test signal.

At step 320, a diagnostic test signal is applied to electrode 400. In one embodiment, the diagnostic signal is a known DC current I that is injected into the electrode. Further, in one embodiment the diagnostic current applied to the electrode comprises a series of oscillating square waves, such as the waveform 700 illustrated in FIG. 7. The signal 700 in FIG. 7 is a continuous series of positive and negative DC currents. For example, as illustrated a first test current at a known level is injected into the sensor for a first time duration 702. Then, a second test current that is substantially equal to but opposite in polarity to the first test current is injected into the sensor for a second time duration 704. By injecting current in this manner, the total average charge to the electrode will be zero for a complete test cycle. For a pH electrode, application of a reverse current discharges capacitance in the electrode and prevents unidirectional ionic migration in the electrode glass.

At step 330, a voltage response of the electrode created by the diagnostic signal is measured. The voltage is measured across the electrode and corresponds to the voltage (V) 610 across terminals 620 and 630 represented in FIG. 6. In one embodiment, voltage 610 is sampled over a time duration that is less than, or substantially less than, a time constant (i.e., time constant $R_2 \cdot C_2$) associated with the electrical characteristics of the pH electrode. In one embodiment, voltage 610 is sampled over a time duration that is less than 50 percent of the time constant associated with the pH electrode. For example, in an electrode having a time constant on the order of 7-8 seconds, a diagnostic signal is applied to the electrode and the voltage response is sampled in approximately 1-3 seconds.

Figure 8:
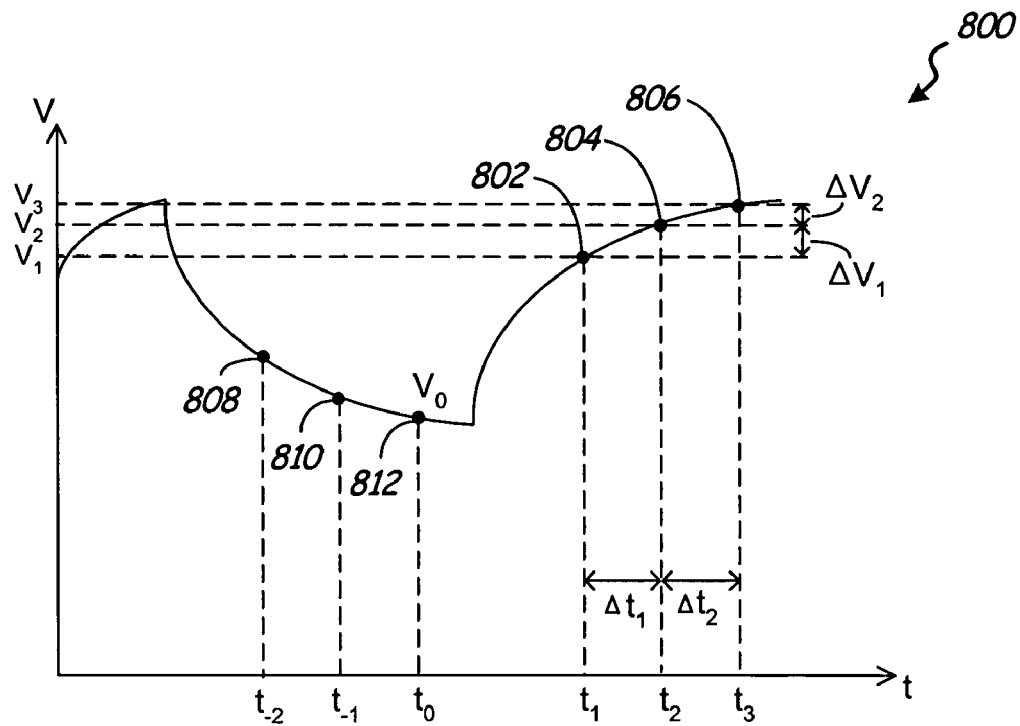
FIG. 8 illustrates an exemplary voltage response of a pH electrode when a diagnostic test signal is applied.

FIG. 8 represents a voltage response 800 of electrode 400 when test signal 700 is applied. In FIG. 8, a plurality of voltages caused by the switched test current are sampled. As illustrated, voltage samples 802, 804, and 806 are positive samples (i.e., samples taking while test signal 700 is positive (i.e., magnitude +I) taken at times $t_1$, $t_2$, and $t_3$. Further, voltage samples 808, 810, and 812 are negative samples (i.e., samples taking while test signal 700 is negative (i.e., magnitude −I) at times $t_{-2}$, $t_{-1}$, and $t_0$. It is noted that in other embodiments, more than or less than three voltage samples can be taken for each application of the switched test signal.

In one embodiment, voltage response 800 (i.e., samples 802-812) is acquired over a time duration that is substantially less than the time constant associated with the electrical characteristics of the pH electrode. In one embodiment, time durations 702 and/or 704 (illustrated in FIG. 7) are less than 50 percent of the time constant associated with the electrical characteristics of the pH electrode. In another embodiment, time durations 702 and 704 together are less than 50 percent of the time constant associated with the electrical characteristics of the pH electrode. Samples 802-812 can be averaged over some multiple of the line voltage periods (i.e. 16.667 or 20 milliseconds).

At step 340, the voltage samples taken at step 330 are utilized to compute the electrode impedance based on the equivalent circuit of the electrode. In accordance with one embodiment, values $t_0$, $\Delta V_1$, $\Delta V_2$, $\Delta t_1$, calculated from the voltage samples are applied to Eq. 5 and/or 6, computed based on the circuit equivalent for the pH electrode. The resulting computation solves the circuit equation for $R_2 C_2$. Further, as discussed above the value of $C_2$ can be set to an arbitrary value K. As such, Eq. 5 becomes:

$$R_2 = \Delta t / [k(\ln \Delta V_1 / \Delta V_2)] \quad \text{(Eq. 7)}$$

In addition to calculating the source impedance of the pH electrode, the sample data from step 330 can also be utilized determine the source voltage produced by the pH sensor, which is indicative of pH level of the solution. In embodiments where the test currents are applied for equal durations and magnitudes, but opposite polarity, the total average charge to the electrode will be zero for a complete test cycle. Source voltage $V_{ph}$ is given as:

$$V_{ph} = ((P_3 + N_3)/2) \quad \text{(Eq. 8)}$$

where $P_3$ is the positive sample taken at time $t_3$ and $N_3$ is the negative sample taken during the prior application of the negative test current (i.e., $t_0$). Thus, $V_{ph}$ represents the average of the voltage changes resulting from the switched test current. Because the time duration between $t_0$ and $t_3$ is substantially less then the time constant of the pH electrode, pH readings are updated more frequently than in conventional systems.

Although the subject matter has been described in language specific to structural features and/or methodological acts, it is to be understood that the subject matter defined in the appended claims is not necessarily limited to the specific features or acts described above as has been determined by the courts. Rather, the specific features and acts described above are disclosed as example forms of implementing the claims and can be varied in a number of ways within the scope of the claims.

What is claimed is:

1. A method of measuring impedance of a pH electrode, the method comprising:
   applying a test current to the pH electrode for a time duration that is less than 50 percent of a time constant that is associated with electrical characteristics of the pH electrode wherein applying a test current includes applying a first test current to the pH electrode for a first time duration and applying a second test current to the pH electrode for a second time duration the second test current being substantially equal to but opposite in polarity to the first test current;
   measuring a voltage response comprising measuring a first voltage response when the first test current is applied to the pH electrode and measuring a second voltage response of the pH electrode while the second test current is applied to the pH electrode;
   calculating an impedance of the pH electrode as a function of the voltage response;
   determining whether the calculated impedance exceeds a maximum allowable impedance; and
   selectively generating a fault signal based upon the step of determining whether the calculated impedance exceeds the maximum allowable impedance; and
   calculating a source voltage of the pH electrode as an average of the first voltage response and the second voltage response, the source voltage being indicative of pH of a solution.

2. The method of claim 1, and further comprising:
   determining a time constant of the pH electrode as a function of an approximated circuit equivalent of the pH electrode, the approximated circuit equivalent being indicative of electrical characteristics of the pH electrode.

3. The method of claim 1, wherein measuring a voltage response comprises sampling a plurality of voltages across the pH electrode.

4. The method of claim 3, wherein sampling a plurality of voltages comprises taking a plurality of voltage samples across the pH electrode during a time duration that is less than approximately three seconds.

5. The method of claim 1, comprising:
   applying the first test current to the pH electrode for a first time duration that is less than 25 percent of a time constant that is associated with electrical characteristics of the pH electrode; and
   applying the second test current to the pH electrode for a second time duration that is less than 25 percent of a time constant that is associated with electrical characteristics of the pH electrode.

6. The method of claim 5 wherein the first and second time durations are substantially similar.

7. The method of claim 1, wherein calculating the impedance of the pH electrode comprises:
   calculating an impedance of the pH electrode as a function of the first voltage response and the second voltage response.

8. The method of claim 1, wherein measuring the first voltage response comprises acquiring a first plurality of voltage samples across the pH electrode when the first test current is applied to the pH electrode, and wherein measuring the second voltage response comprises acquiring a second plurality of voltage samples across the pH electrode when the second test current is applied to the pH electrode.

9. The method of claim 8, wherein each of the first and second plurality of voltage samples comprises three voltage samples taken across the pH electrode.

10. The method of claim 9, wherein the plurality of voltage samples are averaged over multiple line voltage periods.

11. The method of claim 1, wherein calculating an impedance of the pH electrode as a function of the voltage response is performed within a duration that is less than about 50 percent of the time constant that is associated with electrical characteristics of the pH electrode.

* * * * *